(12) United States Patent
Brousmiche et al.

(10) Patent No.: US 11,035,832 B2
(45) Date of Patent: Jun. 15, 2021

(54) METHODS OF ELECTROSPRAY IONIZATION OF GLYCANS MODIFIED WITH AMPHIPATHIC, STRONGLY BASIC MOIETIES

(71) Applicant: WATERS TECHNOLOGIES CORPORATION, Milford, MA (US)

(72) Inventors: Darryl W. Brousmiche, Grafton, MA (US); Matthew A. Lauber, North Smithfield, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 247 days.

(21) Appl. No.: 16/312,760

(22) PCT Filed: Jun. 19, 2017

(86) PCT No.: PCT/US2017/038073
§ 371 (c)(1),
(2) Date: Dec. 21, 2018

(87) PCT Pub. No.: WO2017/222955
PCT Pub. Date: Dec. 28, 2017

(65) Prior Publication Data
US 2019/0219548 A1    Jul. 18, 2019

Related U.S. Application Data

(60) Provisional application No. 62/352,755, filed on Jun. 21, 2016.

(51) Int. Cl.
*G01N 30/06*    (2006.01)
*B01D 15/12*    (2006.01)
(Continued)

(52) U.S. Cl.
CPC ............ *G01N 30/06* (2013.01); *B01D 15/12* (2013.01); *B01D 15/327* (2013.01);
(Continued)

(58) Field of Classification Search
CPC .... G01N 30/06; G01N 30/04; G01N 30/7233; G01N 33/58; G01N 2030/067;
(Continued)

(56) References Cited

U.S. PATENT DOCUMENTS 2,016,962 A    10/1935    Flint et al.
4,003,912 A    1/1977    Franz
(Continued)

FOREIGN PATENT DOCUMENTS

CN    1211622 A    3/1999
CN    1973047 A    5/2007
(Continued)

OTHER PUBLICATIONS

Eoin FJ Cosgrave and Sean M McCarthy, Investigation of the Factors that Contribute to Glycan Separation in HILIC, Business Operations, Pharmaceutical Life Sciences, Waters Corporation (Year: 2014).*
(Continued)

*Primary Examiner* — Jennifer Wecker
*Assistant Examiner* — Jonathan Bortoli
(74) *Attorney, Agent, or Firm* — Kacvinsky Daisak Bluni PLLC

(57) ABSTRACT

Solutions, detection methods and chromatographic systems are provided for electrospray ionization of glycans modified with amphipathic, strongly basic moieties. The solutions for use in electrospray ionization comprise a plurality of glycans having an amphipathic moiety, a basic residue of pKa>5 and a Log P value between 1 and 3, and one or more volatile components selected from the group consisting of an amine,
(Continued)

ammonia, ammonia salt, diethylamine, or trimethylamine. The solutions also have a pH between about 3 to about 6, and ionic strength of between about 0 mM to about 500 mM. The solutions are useful in detecting modified glycans in electrospray ionization and in various chromatographic systems.

20 Claims, 4 Drawing Sheets

(51) Int. Cl.
  *B01D 15/32* (2006.01)
  *B01D 15/38* (2006.01)
  *G01N 33/58* (2006.01)
  *G01N 30/04* (2006.01)
  *G01N 30/72* (2006.01)
  *H01J 49/16* (2006.01)
  *G01N 30/88* (2006.01)

(52) U.S. Cl.
  CPC ......... *B01D 15/3847* (2013.01); *G01N 30/04* (2013.01); *G01N 30/7233* (2013.01); *G01N 33/58* (2013.01); *H01J 49/165* (2013.01); *G01N 2030/067* (2013.01); *G01N 2030/8836* (2013.01)

(58) Field of Classification Search
  CPC ........... G01N 2030/8836; H01J 49/165; B01D 15/12; B01D 15/327; B01D 15/3847
  See application file for complete search history.

(56) References Cited

U.S. PATENT DOCUMENTS

| | | | |
|---|---|---|---|
| 4,068,528 | A | 1/1978 | Gundelfinger |
| 4,138,398 | A | 2/1979 | Richter et al. |
| 5,296,599 | A | 3/1994 | Cohen et al. |
| 5,531,959 | A | 7/1996 | Johnson et al. |
| 6,245,478 | B1 | 6/2001 | Uetani et al. |
| 6,379,971 | B1 | 4/2002 | Schneider et al. |
| 6,632,629 | B2 | 10/2003 | Yang et al. |
| 6,716,634 | B1 | 4/2004 | Myerson |
| 7,074,570 | B2 | 7/2006 | Palmgren et al. |
| 7,148,069 | B2 | 12/2006 | Miyano et al. |
| 7,186,739 | B2 | 3/2007 | Guichard et al. |
| 7,494,815 | B2 | 2/2009 | Shimbo et al. |
| 7,732,378 | B2 | 6/2010 | Thompson et al. |
| 8,124,792 | B2 | 2/2012 | Baginski |
| 8,198,063 | B1 | 6/2012 | Baginski et al. |
| 8,445,292 | B2 | 5/2013 | Baginski |
| 9,658,234 | B2 | 5/2017 | Miyano et al. |
| 10,416,166 | B2 | 9/2019 | Brousmiche et al. |
| 2001/0026929 | A1 | 10/2001 | Yang et al. |
| 2004/0259262 | A1 | 12/2004 | Ishii |
| 2005/0079624 | A1 | 4/2005 | Miyano et al. |
| 2005/0158708 | A1 | 7/2005 | Alroy et al. |
| 2005/0221337 | A1 | 10/2005 | Seeberger et al. |
| 2006/0004220 | A1 | 1/2006 | Hamprecht et al. |
| 2006/0035304 | A1 | 2/2006 | Lebrilla et al. |
| 2006/0286673 | A1 | 12/2006 | Miyano et al. |
| 2007/0141723 | A1 | 6/2007 | Sompuram et al. |
| 2007/0269895 | A1 | 11/2007 | Aebersold et al. |
| 2008/0201095 | A1 | 8/2008 | Yip et al. |
| 2008/0241856 | A1 | 10/2008 | Wong et al. |
| 2008/0315084 | A1 | 12/2008 | Yamada et al. |
| 2009/0050212 | A1 | 2/2009 | Dourdeville et al. |
| 2009/0065687 | A1 | 3/2009 | Gross et al. |
| 2009/0258437 | A1 | 10/2009 | Baginski |
| 2010/0151499 | A1 | 6/2010 | Collins et al. |
| 2010/0171055 | A1 | 7/2010 | Dourdeville |
| 2011/0006237 | A1 | 1/2011 | Tower |
| 2011/0171736 | A1 | 7/2011 | Agnew et al. |
| 2012/0107942 | A1 | 5/2012 | Baginski |
| 2012/0165370 | A1 | 6/2012 | Tang et al. |
| 2013/0112604 | A1 | 5/2013 | Keene et al. |
| 2013/0171658 | A1 | 7/2013 | Fulton et al. |
| 2014/0030732 | A1 | 1/2014 | Staples |
| 2014/0038215 | A1 | 2/2014 | Smart et al. |
| 2014/0178912 | A1 | 6/2014 | Liu et al. |
| 2014/0179011 | A1 | 6/2014 | Brousmiche et al. |
| 2014/0200148 | A1 | 7/2014 | Slade |
| 2014/0227793 | A1 | 8/2014 | Gao et al. |
| 2014/0242709 | A1 | 8/2014 | Brousmiche et al. |
| 2014/0274768 | A1 | 9/2014 | Haab |
| 2014/0350263 | A1 | 11/2014 | Brousmiche et al. |
| 2014/0370614 | A1 | 12/2014 | Liu et al. |
| 2015/0057243 | A1 | 2/2015 | Zhou et al. |
| 2015/0204824 | A1 | 7/2015 | Lauber et al. |
| 2015/0346194 | A1 | 12/2015 | Magnelli et al. |
| 2016/0018409 | A1 | 1/2016 | Higel |
| 2016/0054274 | A1 | 2/2016 | Cormier et al. |
| 2016/0069844 | A1 | 3/2016 | Jackson et al. |
| 2016/0139136 | A1 | 5/2016 | Brousmiche et al. |

FOREIGN PATENT DOCUMENTS

| | | |
|---|---|---|
| CN | 102690833 A | 9/2012 |
| CN | 103918055 A | 7/2014 |
| EP | 0671401 A1 | 9/1995 |
| EP | 2305692 A1 | 4/2011 |
| EP | 2990401 A1 | 3/2016 |
| JP | S59161355 A | 9/1984 |
| JP | S60186502 A | 9/1985 |
| JP | S62195361 A | 8/1987 |
| JP | H09101310 A | 4/1997 |
| JP | H10306075 A | 11/1998 |
| JP | H1180107 A | 3/1999 |
| JP | 2000510854 A | 8/2000 |
| JP | 2000329744 A | 11/2000 |
| JP | 2001526048 A | 12/2001 |
| JP | 2006038674 A | 2/2006 |
| JP | 2012512234 A | 5/2012 |
| JP | 2015091953 A | 5/2015 |
| WO | 9921580 A1 | 5/1999 |
| WO | 02074245 A2 | 9/2002 |
| WO | 2004027388 A2 | 4/2004 |
| WO | 2004086050 A2 | 10/2004 |
| WO | 2006114663 A1 | 11/2006 |
| WO | 2009070233 A1 | 6/2009 |
| WO | 2011038873 A1 | 4/2011 |
| WO | 2011146594 A2 | 11/2011 |
| WO | 2013081581 A1 | 6/2013 |
| WO | 2013084236 A1 | 6/2013 |
| WO | 2013151975 A1 | 10/2013 |
| WO | 2013192530 A2 | 12/2013 |
| WO | 2014085938 A1 | 6/2014 |
| WO | 2014194320 A1 | 12/2014 |
| WO | 2016009077 A1 | 1/2016 |
| WO | 2016069764 A1 | 5/2016 |
| WO | 2016089515 A1 | 6/2016 |

OTHER PUBLICATIONS

Extended European Search Report for Application No. 17767589.9, dated Jan. 30, 2020, 11 pages.
International Search Report and Written Opinion for International Application No. PCT/US17/38073, dated Sep. 12, 2017, 9 pages.
Song, X., et al., "Glycan microarrays of fluorescently-tagged natural glycans", Glycoconjugate Journal, 32:465-473 (2015).
Schwartz, B., et al., "A Kinetic Characterization of the Glycosyltransferase Activity of *Eschericia coli* PBP1b and Development of a Continuous Fluorescence Assay", Biochemistry, 41:12552-12561 (2002).
Bunz, S-C., et al., "Analysis of native and APTS-labeled N-glycans by capillary electrophoresis/time-of-flight mass spectrometry", Analytical and Bioanalytical Chemistry 405:8277-8284 (2013).
Knezevic, A., et al., "High throughput plasma N-glycome profiling using multiplexed labelling and UPLC with fluorescence detection", Analyst, 136:4670 (2011).

(56) References Cited

OTHER PUBLICATIONS

Lauber, M.A. et al., "Rapid Preparation of Released N-Glycans for HILIC Analysis Using a Labeling Reagent that Facilitiates Sensitive Fluorescence and ESI-MS Detection", Analytical Chemistry 87:5401-5409 (2015).
Suzuki,et al, "Comparision of the Sensitivities of Various Derivatives of Oligosacchardies in LC/MS with Fast Atom Bombardment and Elecgtrospray Ionization Interfaces", Analytical Chemistry 68(13):2073-2083 (1996).
International Search Report and Written Opinion for International Application No. PCT/US2017/038073, dated Sep. 12, 2017, 10 pages.
Bioengineering Analysis and Inspection, Wang Furong China Light Industry Press pub. Jun. 30, 2005.
CNOA for application 201580071764.2 dated Feb. 28, 2020 original and translated document, 18 pages.
Fu-Chuan, Li, et al., "Studies on Fluorescent Labeling of Marine Sulfated Polysaccharide 911", Chemical Journal of Chinese Universities, 23(9):1704-1708 (2002) Abstract.
Zailin, W., "Studies on Fluorescent Labeling of Several Fungal Polysaccharides", Chinese Master's Thesis, Agriculture Science and Technology, No. 5 (2013).
Takeda, K., et al., Convenient Methods for Syntheses of Active Carbamates, Ureas and Nitrosoureas Using N,N'-Disuccinimido Carbonate (DSC), Tetrahedron Letters 24(42):4569-72 (1983) Abstract.
Tarentino, A.L., et al., "2-Iminothiolane: A Reagent for the Introduction of Sylphydryl Groups into Oligosaccharides Derived from Asparagine-Linked Glycans", Glycobiology 3(3):279-285 (1993) Abstract.
Tousi "The Pursuit of Cancer Biomarkers: Liquid Chromatography and Mass Spectrometry 1-13 Platforms for Glycomic Characterization of Biospecimens" Northeastern University, Jul. 16, 2013.
Ullmer, R., et.al., "Derivatization by 6-aminoquinolyl-N-hydroxysuccinimidyl Carbamate for Enhancing the Ionization Yield of Small Peptides and Glycopeptides in Matrix-Assisted Laser Desorption/Ionization and Electrospray Ionization Mass Spectrometry", Rapid Communications in Mass Spectrometry pp. 1469-1479 (2006).
Van Wandelen, C., et al., "Using Quaternary High-Performance Liquid Chromatography Eluent Systems for Separating 6-Aminoquinolyl-N-Hydroxysuccinimidyl Carbamate-Derivatized Amino Acid Mixtures", Journal of Chromatography A, 763:11-22 (1997).
Vasilevich, N., et al., "Conversion of O-Succinimidyl Carbamates to N-(O-Carbamoyl)-Succinmonoamides and Ureas: Effects of N-Substituents and Reaction Conditions on the Reaction Pathway", Tetrahedron Letters 43:6649-6652 (2002) Abstract.
Voet, "Biochemistry" Second Edition, John Wiley & Sons, Inc. 1995, Chapters 4, 5. Abstract.
Vollhardt, "Organic Chemistry Structure and Function," Third Edition, W. H. Freeman and Company, 1999, Chapters 14, 20, 21, 26. Abstract.
Wada, Y., et al., "Comparison of the Methods for Profiling Glycoprotein Glycans—HUPO Human Disease Glycomics/Proteome Initiative Multi-Institutional Study", Glycobiology 17(4):411-422 (2007).
Walker et al., Hydrophobic Derivatization of N-linked Glycans for Increased Ion Abundance in Electrospray onization Mass Spectrometry, J Am Soc Mass Spectrom 2011; 22(8): 1309-17.
Waters Corporation "GlycoWorks High-Throughput Sample Preparation Kit" (Sep. 2013).
Watson, "Introduction to Mass Spectrometry" Raven Press, New York 1985, Chapters 1 and 4. Abstract.
Wei, W-J., et al., "Study on N-Hydroxyphthalimide as Blocking Agent for Isocyanates", Journal of Applied Polymer Science 84:1346-1352 (2002).
Wuhrer, M., et al., "Nano-Scale Liquid Chromatography-Mass Spectrometry of 2-Aminobenzamide-Labeled Oligosaccharides at Low Femtomole Sensitivity", International Journal of Mass Spectrometru 232:51-57 (2004).
Yates, "Peptide Mass Maps: A Highly Informative Approach to Protein Identification," Analytical Biochemistry 1993, 214: 397-408.
Yodoshi, M., et al: "Optimized conditions for high-perfonnance liquid chromatography analysis of oligosaccharides using 7-amino-4-methylcoumarin as a reductive amination reagent", Journal of Chromatography A Elsevier, Amsterdam, NL, vol. 1203, No. 2, pp. 137-145, Sep. 5, 2008.
Yost, "Triple Quadrupole Mass Spectrometry for Direct Mixture Analysis and Structure Elucidation," Analytical Chemistry 1979, 51(12):1251A-1264A. Abstract.
Yu Y. Q., "N-linked Glycan Characterization and Profiling: Combining the Power of Accurate Mass, Reference Glucose Units, and UNIFI Software for Confident Glycan Assignments," Waters, Application Note (2013) 10 pages.
Yu Y.Q., et al., "A Rapid Sample Preparation Method for Mass Spectrometric Characterization of N-linked Glycans", Rapid Communications in Mass Spectrometry 19:2331-2336 (2005).
Zhang Li et al., "Practical Guidance of Detection by Separation", Press of University of Science and Technology of China, Jan. 2013, p. 55.
Chapter 2—Norepinephrine (NPL cited during examination procedure) Jul. 16, 2020.
Yang et al., "Solid-phase glycan isolation for glycomics analysis", Proteomics Clin Appl. Dec. 2012; 6(0): 596-608. doi:10.1002/prca.201200045 (Year: 2012).
Johannesen et al. "Glycan analysis via derivatization with a fluorogenic pyrylium dye", Carbohydrate Research, 352:94-100 (2012) Abstract.
Extended European Search Report for Application No. EP20188814.6, dated Oct. 2, 2020, 7 pages.
Ahn J., et al., "Separation of 2-aminobenzamide labeled glycans using hydrophilic interaction chromatography columns packed with 1. 7 μm sorbent," Journal of Chromatography B, 878: 403-8 (2010).
Anumula et al., "High Resolution and High Sensitivity Methods for Oligosaccharide Mapping and Characterization by Normal Phase High Performance Liquid Chromatography Following Derivitization with Highly Flourescent Anthranilic Acid", Glycobiology 8(7):685-694 (1998).
Author unknown, Best Practices in the Analysis of Rapifluor-MS Labeled Glycans Using the Acquity QDa Detector 5 Performance Model), Waters [online] Mar. 2016 While Paper [retrieved on Apr. 1, 2020]. Retrieved from the internet URL: https://www.gimite.com/file/720005655en.pdf, 19 pages.
Bartlet-Jones, "Peptide ladder sequencing by mass spectrometry using a novel, volatile degradation reagent," Rapid Commun. Mass Spectrom. 1994, 8, 737-742. Abstract.
Bereman et al., Increasing the hydrophobicity and electrospray response of glycans through derivatization with novel cationic hydrazides, Chem Commun (Camb) 2010; 26 (2): 237-9.
Black, S.D., et al., "Simple, Rapid, and Highly Efficient Separation of Amino Acid Phenylthiohydantoins by Reversed-Phase High-Performance Liquid Chromatography", Analytical Biochemestry 121:281-285 (1982).
Block et al., "2050P: HPLC/MS Analysis of Amino Acids: The Use of 6-Aminoquinolyl-N-Hydroxy-Succinimidyl Carbamate Derivatives", Poster presented at Pittsburgh Conference, Mar. 1999.
Block, E., et al., "2050P: HPLC-MS Analysis of Amino Acids", Abstract presented at Pittsburgh Conference, Mar. 1999.
Block, E.H., "LC/MS Application Notes: The Use of 6-Aminoquinolyl N Hydroxy Succinimidyl Carbamate Derivatives for HPLC/MS Analysis of Amino Acids", Presentation at Pittsburgh Conference, Mar. 1999.
Block, E.H., "The Use of 6-Aminoquinolyl-N-Hydroxy Succinimidyl Carbamate Derivatives for HPLC/MS Analysis of Amino Acids", AMD35 Waters Alliance LC/MS System 2000.
Brancia, "Improved matrix-assisted laser desorption/ionization mass spectrometric analysis of tryptic hydrosylates of proteins following guanidation of lysine-containing peptides," Rapid Commun. Mass Spectrom. 14, 2070-2073 (2000) Abstract.
Briggs, J.B., et al., "An analytical system for the characterization of highly heterogeneous mixtures of N-linked oligosaccharides", Analytical Biochemistry, 389:40-51 (2009).

(56) References Cited

OTHER PUBLICATIONS

Brophy, "Electron Impact and chemical ionization mass spectra of aryl ureas," Organic Mass Spectrometry, vol. 14, No. 7, 1979, 379-386 Abstract.
Buku, "2,3-trans-3,4-trans-3,4-Dihydroxy-L-proline: An Amino Acid in Toxic Peptides of *Amanita virosa* Mushrooms," Proc. Natl. Acad. Sci. USA, 1980, 77(5): 2370-2371.
Busto, "Solid phase extraction of biogenic amines from wine before chromatographic analysis of their AQC derivatives," J. Liq. Chrom. & Rel. Technol. 1997, 20(5), 743-755 Abstract.
Byrnes, "6-Aminoquinoline as a Fluorogenic Leaving Group in Peptide Reactions: A New Fluorogenic Substrate for Chymotrypsin," Anal. Biochem. 116, 408-413 (1981) Abstract.
Campbell M. P., et al., "GlycoBase and autoGU: tools for HPLC-based glycan analysis," Bioinformatics, 24 (9): 1214-1216, (2008).
Casoli, A., et al., "Use of High-Performance Liquid Chromatography for the Determination of Amino Acids in Sparkling Wines", Am J Enol Vitic 33(3):135-139 (1982).
Cech and Enke, "Relating Electrospray Ionization Response to Nonpolar Character of Small Peptides," Anal. Chem. 2000, 72:2717-2723. Abstract.
Chalmers, "Advances in Mass Spectrometry for Proteome Analysis," Current Opinion in Biotechnology 2000, 11: 384-390. Abstract.
Kurita, K., et al., "Synthesis and Properties of Polyurethanes Derived from bis-N-Hydroxyimides and Diisocyanates", Journal of Polymer Science 17:1619-1629 (1979).
Lauber et al., Optimization of GlycoWorks HILIC SPE for the Quantitative and Robust Recovery of N-Linked Glycans from mAb-Type Samples. Waters Application Note. (2013).
Chezal, J-M., et al. "Evaluation of Radiolabeled (Hetero)Aromatic Analogues of N-(2-diethylaminoethyl)-4-iodobenzamide for Imaging and Targeted Radionuclide Therapy of Melanoma" J. Med. Chem. 51:3133-3144 (2008).
Lawrence, "Derivatization in Chromatography Introduction, Practical Aspects of Chemical Derivatization in Chromatography," Journal of Chromatographic Science 1979, 17:113-114. Abstract.
Li De et al.,"Techniques of Biomolecule Scientific Experiments", Hunan Science and Technology Press, Nov. 2001, the 1st edition, p. 32-33.
Liu et al., Investigation of Sample Preparation Artifacts Formed during the Enzymatic Release of N-Linked Glycans prior to Analysis by Capillary Electrophoresis. Anal. Chem. 2009; 81: 6823-6829.
Liu, H., et al., "Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis", Journal of Chromatograpjy A, 828:383-395 (1998).
Liu, H., et al., "Femtomole Peptide Mapping by Derivatization, High-Performance Liquid Chromatography, and Fluorescence Detection", Analytical Biochemistry 294:7-18 (2001). Abstract.
Liu, Hongji, et.al.; "Homogeneous Fluorescent Derivatization of Large Proteins", Journal of Chromatography A, 927: 77-89 (2001).
Louris, "New Scan Modes Accessed with a Hybrid Mass Spectrometer," Anal. Chem. 1985, 57, 2916-2924. Abstract.
Ma, "Determination of Midazolam and its Metabolites in Serum Microsamples by High-Performance Liquid Chromatography and its Application to Pharmacokineics in Rats," J Chromatography B Biomed Appl. 1996, 682 (1):109-113. Abstract.
Marino et al., "A Systematic Approach to Protein Glycosylation Analysis: A Path Through the Maze", Nature Chemical Biology 6:713-723 (2010).
Martinez-Force, E., et al., "Separation of O-Phthalaldehyde Derivatives of Amino Acids of the Internal Pool of Yeast by Reverse-Phase Liquid Chromatography", Biotechnology Technique 5(3):209-214 (1991).
Mazzocchi, Paul et al., "A Photochemical Route to Pyrrolo[1,4]Benzodiazepine Antitumor Antibiotics" Heterocycles 23 (7):1603-1606 (1985).
McLafferty, "Interpretation of Mass Spectra," Fourth Edition, University Science Books, Sausalito, CA 1993, Chapter 1. Abstract.

Mechref et al., Quantitative Glycomics Strategies, Mol Cell Proteomics 2013, 12 (4) 874-84.
Morpugo, "N-hydroxysuccinimide carbonates and carbamates are useful reactive reagents for coupling ligands to lysines on proteins," J. Biochem. Biophys.Methods 38 (1999), 17-28.
Nakashima, "Study on π-π Interaction in High Performance Liquid Chromatography," J. Liq. Chrom. Rel. Technol. 2000, 23(16), 2533-2540 Abstract.
Nimura, "Detection reagents used for high performance liquid chromatography," Pharmacia (1981) 17(8):707-709.
Nimura, N., et al., "Activated Carbamate Reagent as Derivatizing Agent for Amino Compounds in High-Performance Liquid Chromatography", Analytical Chemistry 58:2372-2375 (1986).
Okamoto, "Sensitive Detection and Structural Characterization of Trimethyl(p-aminophenyl)-ammonium-derivatized Oligosaccharides by Electrospray Ionization-Mass Spectrometry and Tandem Mass Spectrometry," Rapid Communications in Mass Spectrometry, 1995, 9, 641-643. Abstract.
Pall Life Sciences "AcroPrep™ Advance Filter Plates" Pall Corporation (Mar. 2013) p. 7, col. 2, 10 Table AcroPrep Advance 96-Well Filter Plates for Ultrafiltration.
Park, S., et al., "Regioselective Covalent Modification of Hemoglobin in Search of Antisickling Agents", J Med Chem 46:936-953 (2003) Abstract.
Paschinger, K., et al., "Analysis of zwillerionic and anionic N-linked glycans from invertebrates and protisls by mass spectrometry", Glycoconjugate Journal, 33(3):273-283 (2016).
Pettersson et al., Chemical Stability of Reversed Phase High Performance Liquid Chromatography Silica under Sodium Hydroxide Regeneration Conditions, J Chromatogr A 2007; 1142 (1 ): 93-7.
Piepponen, T.P., et al., "Rapid and Sensitive Step Gradient Assays of Glutamate, Glycine, Taurine and y-Aminobutyric Acid by High-Performance Liquid Chromatography-Fluorescence Detection with o-Phthalaldehyde-Mercaptoethanol Derivatization With an Emphasis on Microdialysis Samples", Journal of Chromatography B, 757:277-283 (2001).
Pubchem CID: 43450869 Create Date: Jul. 21, 2009.
Qu, Y., et al., "Structural analysis of N- and O-glycans using ZIC-HILIC/dialysis coupled to NMR detection", Fungal Genetics and Biology, 72:207-215 (2014).
Quirke, "Chemical Derivatization for Electrospray Ionization Mass Spectrometry. 1. Alkyl Halides, Alcohols, Phenols, Thiols, and Amines," Anal Chem. 1994, 66, 1302-1315. Abstract.
Rasmussen, "The nomenclature of fused-ring arenes and heterocycles: a guide to an increasingly important dialect of organic chemistry," ChemTexts, 2016, 2(16), 1-13.
Reubsaet, "Characterisation of π-π interactions which determine retention of aromatic compounds in reversed-phase liquid chromatography," Journal of Chromatography A, 1999, 841, 147-154. Abstract.
Roth, "Charge Derivatization of Peptides for Analysis by Mass Spectrometry," Mass Spectrometry Reviews 1998, 17:255-274 Abstract.
Rudd, "Rapid, sensitive sequencing of oligosaccharides from glycoproteins," Current Opinion in Biotechnology 1997, 8:488-497.
Ruhaak et al. Glycan Labeling Strategies and their use in Identification and Qualification, Anal Bioanal Chem 2010, 397 (8), 3457-81.
Saurina, J., et al., "Chromatographic Determination of Amino Acids by Pre-Column Derivatization Using 1,2-Napthoquinone-4-Sulfonate As Reagent", Journal of Chromatography A, 740:21-30 (1996).
Schmeer, K., et al., "Compositional Analysis of the Phenylthiocarbamyl Amino Acids by Liquid Chromatography-36 Atmospheric Pressure Ionization Mass Spectrometry with Particular Attention to the Cyst(e)ine Derivatives", Journal of Chromatography A,691:285-299 (1995).
Schmidt, C.J., et al., "Amino Acid Profiling of Protein Hydrolysates Using Liquid Chromatography and Fluorescence Detection", Journal of Liquid Chromatography 2(7):1031-1045 (1979).
Schwartz, "Multistage mass spectrometry: Scan modes and new instrumentation" Dissertation 1989.
Schwartz, "Systematic Delineation of Scan Modes in Multidimensional Mass Spectrometry," Anal. Chem. 1990, 62:1809-1818 Abstract.

(56) References Cited

OTHER PUBLICATIONS

Search Report for GB1509402.2 dated Mar. 1, 2016.
Shimbo, "Multifunctional and Highly Sensitive Precolumn Reagents for Amino Acids in Liquid Chromatography/Tandem Mass Spectrometry," Anal. Chem. 2009, 81, 5172-5179. Abstract.
Snyder, "Introduction to Modern Liquid Chromatography," Second Edition, John Wiley & Sons, Inc. 1979, Introduction, Chapters 2, 4, 13, 14, 17. Abstract.
Synder, "Practical HPLC Method Development," Second Edition, John Wiley & Sons, Inc. 1997, Chapters 3, 4. Abstract.
Spengler, "Peptide sequencing of charged derivatives by postsource decay MALDI mass spectrometry," Int. J. Mass Spectrom. Ion Processes 1997, $^{169}/_{170}$, 127-140. Abstract.
Statement of grounds appeal for European patent application No. 15180680.9, dated May 20, 2020, 4 pages.
Stockmann, "Ultrahigh Throughput, Ultrafiltration-Based NGlycomics Platform for Ultraperformance Liquid Chromatography (ULTRA3)," Anal. Chem. 2015, 87, 8316-8322. Abstract.
Struwe et al. 'Aminoquinolines as fluorescent labels for hydrophilic interaction liquid chromatography of oligosaccharides', Biological Chemistry, 2012, vol. 393, pp. 757-765.
Summons to attend oral proceedings pursuant to Rule 115(1) EPC for Application No. EP15180680.9, dated Jul. 18, 2019, 4 pages.
Summons to attend oral proceedings pursuant to Rule 115(1) EPC for Application No. EP15180680.9, dated Jun. 17, 2019, 9 pages.
Supplementary European Search Report, EP12836127.6 dated Sep. 12, 2014 and Response dated Mar. 19, 2015.
Ciucanu et al., A Simple and Rapid Method for the Permethylation of Carbohyrates, Carbohydr. Res. 1984, 131, 209-217.
International Search Report and Written Opinion for International application No. PCT/US2017/038072, dated Oct. 3, 2017, 9 pages.
International Search Report and Written Opinion for International application No. PCT/GB2016/051605 dated Sep. 15, 2016.
International Search Report and Written Opinion for International Application No. PCT/US2017/014790, dated Apr. 27, 2017.
International Search Report and Written Opinion for International application No. PCT/US15/60326, dated Feb. 2, 2016, 6 pages.
International Search Report and Written Opinion for International application No. PCT/US2012/057996 dated Jan. 31, 2013.
Isbell, H.S. et al., "Effect of pH in the Mutarotation and Hydrolysis of Glycosylamines", JAGS letter to editor, 72:1043-1044 (1950).
Iwaki, "Activated carbamate reagent chiral derivatizing agent for liquid chromatographic optical resolution of enantiomeric amino compounds," Chromatographia 1987, 23(12), 899-902 Abstract.
Iwaki, "Amino acid analysis by reversed-phase high-performance liquid chromatography automatic pre-column derivatization with activated carbamate reagent," Journal of Chromatography, 407 (1987) 273-279 Abstract.
Jupille, "UV-Visible Absorption Derivatization in Liquid Chromatography," Journal of Chromatographic Science 1979, 17:160-167. Abstract.
Keough, "Atmospheric Pressure Matrix-Assisted Laser Desorption/Ionization Ion Trap Mass Spectrometry of Sulfonic Acid Derivatized Tryptic Peptides," Rapid Communications in Mass Spectrometry 2001, 15: 2227-2239. Abstract.
Kimzey, Michael et al., "Development of an Instant Glycan Labeling Dye for High Throughput Analysis by Mass Spectrometry", Prozyme Advancing Glycosciences, May 13, 2015, 4 pages.
Kinzel, O., et al., "Identification of MK-5710 ((8aS)-8a-methyl-1,3-dioxo-2-((1S,2R)-2-phenylcyclopropyl]-N-(1-phenyl-1H-pyrazol-5-yl)hexahydro-imidazo [1,5-a]pyrazine-7(1 H)-carboxamide), a potent smoothened antagonist for use in Hedgehog pathway dependent malignancies, Part 2", Bioorganic & Medicinal Chemistry Letters 21:4429-4435 (2011).
Klapoetke, S, et al., "The Evaluation of a Novel Approach for the Profiling and Identification of N-linked Glycans With a Procainamide Tag by HPLC With Fluorescent and Mass Spectrometric Detection", Journal of Pharmaceutical and Biomedical Analysis 53(3):315-324 ( 2010).

Kuster, B., et al: "Structural Determination of N-linked carbohyrdrates by matrix-assisted laser desorption/ionization-mass spectrometry following enzymatic release within sodium dodecyl sulphate-polyacrylamide electrophoresis gels: application to species-specific glycosylat", Electrophoresis: Liquid Phase Separation Techniques: Microfulidics, Naoanalysis, Proteomics, Wiley Interscience, DE, vol. 19, No. 11, pp. 1950-1959, Aug. 1, 1990.
EP12836127.6 Opposition Communication dated Jul. 23, 2019. 10 pages.
Communication pursuant to Article 94(3) EPC in European Patent Application No. 17815987. 7, dated Dec. 4, 2020, 5 pages.
Amendment and Response filed in U.S. Appl. No. 12/365,880, filed Feb. 4, 2009, dated Sep. 9, 2011, 17 pages.
Communication pursuant to Article 94(3) EPC, for Application No. EP17820918.5, dated Nov. 26, 2020, 5 pages.
Neville, D.C.A., et al., "Development of a Single Column Method for the Separation of Lipid- and Protein-Derived Oligosaccharides", Journal of Proteome Research, 8(2):681-687 (2009).
Decision on Rejection, Chinese Application No. 201280047599.3, dated Dec. 5, 2016, Original and translated.
Heindel, N.D., et al., "Diaminoquinoline antimalarials", J. Med. Chem. 12(5):797-801 (1969).
Non-Final Office Action, U.S. Appl. No. 14/193,418, dated Nov. 15, 2016.
Non-Final Office Action, U.S. Appl. No. 14/342,131, dated Nov. 4, 2016.
Notice of Rejection, JP Application No. 2014-533416, dated Jan. 10, 2017. Original and Translated.
Office Action, U.S. Appl. No. 14/458,760, dated Apr. 12, 2017.
Response to EP Communication with extended search report, EP Application No. 15180680.9, dated Sep. 2, 2016.
Response to Non-Final Office Action, U.S. Appl. No. 14/342,131 dated Feb. 6, 2017.
Response to Non-Final Office Action, U.S. Appl. No. 14/193,418, dated Feb. 15, 2017.
Response to notice of opposition for EP Patent No. 2761296 filed Oct. 19, 2018.
Response to Office Action, U.S. Appl. No. 14/458,760, dated Jun. 12, 2017.
Response to Restriction Requirement, U.S. Appl. No. 14/342,131 dated Sep. 28, 2016.
Restriction Requirement, U.S. Appl. No. 14/342,131, dated Aug. 17, 2016.
Saurina, J., et al., "Determination of Amino Acids by Ion-Pair Liquid Chromatography With Post-Column Derivatization Using 1,2-Naphthoquinone-4-Sulfonate", Journal of Chromatography A,676:311-319 (1994).
Notice for Reasons for Rejection, dated Jul. 23, 2012, in Japanese Application No. 2009-269796 OD and Trans.
Extended European Search Report for EP Application No. 17815987. 7, dated Dec. 16, 2019, 8 pages.
Registry File from STN for compound RN 1915940-97-4, entered on STN May 23, 2016, downloaded Sep. 8, 2020 (Year: 2016).
Registry File from STN for compound RN 1919202-16-6, entered on STN May 27, 2016, downloaded Sep. 8, 2020 (Year: 2016).
Registry File from STN for compound RN 1970079-84-5, entered on STN Aug. 9, 2016, downloaded Sep. 8, 2020 (Year: 2016).
Registry File from STN for compound RN 1975675-34-3, entered on STN Aug. 19, 2016, downloaded Sep. 8, 2020 (Year: 2016).
Registry File from STN for compound RN 1977407-60-5, entered on STN Aug. 22, 2016, downloaded Sep. 8, 2020 (Year: 2016).
West, C., et al., "Porous Graphitic Carbon: a Versatile Stationary Phase for Liquid Chromatography", J Chromatogr A 1217(19):3201-16 (2010).
Cline et al., "The Aminolysis of N-Hydroxysuccinimide Esters. A Structure-Reactivity Study", J Am Chem Soc 109 (10):3087-3091 (1987).
Cohen, "Clearing the Hurdle of High Sensitivity in Biopharmaceutical Research," LC GC North America 1999, 17(4S): S9-S16.
Cohen, S. A., et al.,"Compositional Protein Analysis Using 6-Aminoquinolyl-N-Hydroxysuccinimidyl Carbamate, a Novel Derivatization Reagent", Techniques in Protein Chemistry IV pp. 289-298 (1993).

(56) References Cited

OTHER PUBLICATIONS

Cohen, S. A., et al., "Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography", Analytical Biochemistry 211:279-87 (1993).
Communication of a notice of opposition for EP Patent No. 2761296 dated Jun. 5, 2018.
Communication pursuant to Article 94(3) EPC for Application No. EP17188121.2, dated Sep. 14, 2020, 3 pages.
Communication pursuant to Article 94(3) EPC, dated Apr. 17, 2019, for Application No. EP15855907.0, 4 pages.
Cook et al., Development and Qualification of an Antibody Rapid Deglycosylation Method, Biologicals 2012; 40 (2):109-17.
European Search Report and Written Opinion dated Feb. 2, 2016 regarding patent application No. EP 15180680.9, 7 pages.
Cooper, D., et al., "LC-MS/MS Analysis of AccQ-Tag Derivatised Amino Acids", Micromass UkK Limited pp. 1-7 (2000).
Cooper, D., et al., "LC-MS/MS Analysis of AccQ-Tag Derivatised Amino Acids, Micromass Application Brief", Sep. 2000 and Jun. 2000.
Cooper, D., et al., "LC-MS-MS Analysis of Amino Acids Using AccQ-Tag derivatisation, Application Brief AB25", Micromass June and Sep. 2000.
Covey, "Liquid Chromatography/Mass Spectrometry," Analytical Chemistry 1986, 58(14):1451A-1461A. Abstract.
Darren L. Holmes, Eric M. Smith, and James S. Nowick "Solid-Phase Synthesis of Artificial beta-Sheets" Journal of American Chemical Society 119: 7665-7669 (1997).
De Antonis, K. M., et al., "High-Performance Liquid Chromatographic Analysis of Synthetic Peptides Using Derivatization with 6-Aminoquinolyl-N-Hydroxysuccinimidyl Carbamate", Analytical Biochemistry 223:191-197 (1994).
De Hoffmann, "Mass Spectrometry, Principles and Applications," Second Edition, John Wiley Sons Ltd. 2001, Introduction, Chapters 1, 3, and 7. Abstract.
De Hoffmann, "Tandem Mass Spectrometry: a Primer," J. Mass Spec. 1996, 31, 129-137. Abstract.
Dell, "Fast Atom Bombardment Mass Spectrometric Strategies for Characterizing Carbohydrate-containing Biopolymers," Biomedical and Environmental Mass Spectrometry, 1988, 16, 19-24. Abstract.
Dextran Calibration Ladder Standard. Waters (2012), 3 pages.
Dextran Calibration Ladder. Waters. Product Solution (2013) 3 pages.
European Search Report for Application No. 15855907.0, dated Jul. 6, 2018, 12 pages.
EP Communication pursuant to Article 94(3) EPC, EP Application No. 12836127.6, dated Sep. 26, 2016.
EP Communication under Rule 71(3) EPC, EP Application No. 12836127.6, dated Mar. 15, 2017.
EP Communication with extended search report, EP Application No. 15180680.9, dated Feb. 2, 2016.
European Search Report and Written Opinion dated Aug. 26, 2014 regarding patent application No. EP12836127.6, 6 pages.
Expert Declaration by Prof. Ulf Diederichsen submitted in the opposition proceedings relating to the European patent EP2761296B1, dated Jul. 23, 2019, 7 pp.
Extended European Search Report and Written Opinion for EP Application No. 15855907.0 dated Mar. 19, 2018, 10 pages.
Extended European Search Report for Application No. EP17820918.5, dated Jan. 28, 2020, 7 pages.
Extended European Search Report, EP 12836127.6, dated Aug. 26, 2014.
Fekkes, "State-Of-The-Art of High-Performance Liquid Chromatographic Analysis of Amino Acids in Physiological Samples," Journal of Chromatography B. 1996, 682(1):3-22.
Field, B., et al, Chromatography Forum: LC-MS & GC-MS Archives: AAA LC-MS [online] 2003 [retrieved on Jan. 30, 2003]. Retrieved from Internet URL http://www. lcresources. com/d iscus/messages/5135/3143. html, 6 pages.
GlykoPrep™ Instant AB now fully commercialized. http://www.europa-bioproducts.com/latest.aspx?id=14 {accessed Sep. 8, 2014).
Gong et al., N-Glycosylamine-Mediated Isotope Labeling for Mass Spectrometry-Based Quantitative Analysis of Ncinked Glycans. Anal Bioanal Chem 2013; 405: 5825-31.
Guichard, G., et al., "Effective Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas", Journal of Org Chem 64:8702-8705 (1999).
Guile G. R., et al., "A Rapid High-Resolution High-Performance Liquid Chromatographic Method for Separating Glycan Mixtures and Analyzing Oligosaccharide Profiles," Analytical Biochemistry, 240: 210-226, (1996).
H. R. Liang, et al., "Quantitative determination of endogenous sorbitol and fructose in human nerve tissues by atmospheric-pressure chemical ionization liquid chromatography tandem mass spectrometry", Rapid Communications in Mass Spectrometry, 19(16):2284-2294, Aug. 30, 2005. Abstract.
Harvey, Electrospray Mass Spectrometry and Fragmentation of N-Linked Carbohydrates Derivatized at the Reducing Terminus, J Am Soc Mass Spectrom 2000, 11 (10), 900-15.
Harvey et al., Proposal for a standard system for drawing structural diagrams of N- and O-linked carbohydrates and related compounds, Proteomics 2009; 9 (15): 3796-3801.
Harvey, D., "Identification of protein-bound carbohydrates by mass spectrometry" Proteomics 1:311-328 (2001).
Heinze-Krauss, I., et al., "Structure-Based Design of β-Lactamase Inhibitors. 1. Synthesis and Evaluation of Bridged Monobactams", Journal of Med Chem 41:3961-3971 (1998) Abstract.
Hermanson, "Bioconjugate Techniques," 1996, Chapter 8. Abstract.
Higashi, T., et al., "Derivatization of Neutral Steroids to Enhance Their Detection Characteristics in Liquid Chromatography-Mass Spectrometry", Anal Bioanal Chem 378:875-882 (2004).
Higuchi, K., et al., "Chemistry of Succinimido Esters. IV*1. A Facile Preparation of N-Succinimidyl Carboxylates Using N, N'-Disuccinimidyl Carbonate", Oil Chemistry, 36(1):16-20 (1987).
Hirai, "Development of a new fluorescence labeling reagent succinimido-2-fluorenylcarbamate for highly sensitive detection of N-solanesyl-N,N-bis(3,4-dimethoxybenzyl) ethanediamine by HPLC," Anal. Chem. 1991, 40(5):233-238. Abstract.
Hochleitner, E.O., et al., "Determination of the Stoichiometry of Protein Complexes Using Liquid Chromatography with Fluorescence and Mass Spectrometric Detection of Fluorescently Labeled Proteolytic Peptides", Proteomics 4:669-676 (2004).
Hossler et al., "Optimal and Consistent Protein Glycosylation in Mammalian Cell Culture", Glycobiology 19(9):936-949 (2009).
HP Primer Hewlett Packard, Basics of LC/MS: A Primer. 1998.
International Preliminary Report on Patentability, for International application No. PCT/US2012/057996, dated Apr. 1, 2014, 5 pages.
International Search Report and Written Opinion for International App. No. PCT/US15/57848, dated Feb. 5, 2016, 5 pages.
International Search Report and Written Opinion for International Application No. PCT/US2017/038070, dated Sep. 29, 2017, 10 pages.
CNOA for Patent Application No. 201780053453.2 dated Feb. 4, 2021, original and translated document 24 pages.
Zhang Y., ed., Biological Sample Library Establishment and Practice, p. 102 Sun Yat-Sen University Press (Oct. 2013).
Huang, R., ed., Analytical Chemistry, National Defense Science and Technology University Press pp. 146-150 (Mar. 2014).

\* cited by examiner

METHODS OF ELECTROSPRAY IONIZATION OF GLYCANS MODIFIED WITH AMPHIPATHIC, STRONGLY BASIC MOIETIES

CROSS-REFERENCE TO RELATED APPLICATIONS

This application is a national phase filing claiming the benefit of and priority to International Patent Application No. PCT/US2017/038073, filed on Jun. 19, 2017, which claims priority to U.S. Provisional Patent Application No. 62/352,755 filed Jun. 21, 2016, incorporated herein by reference.

BACKGROUND

When subject to electrospray ionization, labeled glycans in formic acid based mobile phases are prone to degradation via in-source fragmentation, even when relatively gentle mass spectrometry source conditions are employed and for glycans modified with strongly basic residues. A need exists, therefore, for higher sensitivity, less ambiguous MS analysis for these labeled glycans to be obtained.

SUMMARY OF THE INVENTION

Provided herein are solutions, methods and systems for electrospray ionization of glycans which have been modified with amphipathic, strongly basic moieties. The solution for use in electrospray ionization comprises a plurality of glycans having an amphipathic moiety and a basic residue of pKa>5, and one or more volatile components selected from the group consisting of an amine, ammonia, ammonia salt, diethylamine, or trimethylamine. In an embodiment, the solution has a pH between about 3 to about 6, and ionic strength of between about 0 mM to about 500 mM. In an embodiment, the solution can further comprise a solvent. In an embodiment, the solvent can be acetonitrile, methanol, tetrahydrofuran, ethanol or isopropyl alcohol. Furthermore, in an embodiment, the glycan is modified with an amphipathic, strongly basic moiety has a Log P value between about 1 and about 3. In an embodiment, the amphipathic, strongly basic moiety has a pKa value greater than 6. In an embodiment, the basic residue is a tertiary amine. In an embodiment, the amphipathic moiety of the glycan is imparted by RFMS. In an embodiment, the glycans can be an O-glycan or an N-glycan.

Also, provided herein are chromatographic systems for glycan analysis that include a solution having a plurality of glycans modified to include an amphipathic moiety and basic residue of pKa>5, and one or more volatile components selected from the group consisting of an amine, ammonia, ammonia salt, diethylamine, or trimethylamine, and a chromatographic device comprising a hydrophobic stationary phase. In an embodiment, the solution has a pH between about 3 to about 6, and ionic strength of between about 0 mM to about 500 mM. In an embodiment, the chromatographic system has a reversed-phase retention mechanism. In an embodiment, the chromatographic device is a combination of reversed-phase chromatography and mixed mode reversed-phase chromatography. In an embodiment, the glycans can be an O-glycan or an N-glycan.

Further provided herein are methods of detecting a glycan comprising the steps of: (1) providing a sample having a glycan; (2) forming a derivatized glycan in the sample wherein the glycan is modified to include an amphipathic moiety and basic residue of pKa greater than 5; (3) separating the derivativized glycans in a chromatographic device and in a solution comprising one or more volatile components selected from the group consisting of an amine, ammonia, ammonia salt, diethylamine, or trimethylamine, the solution having a pH between about 3 to about 6, and ionic strength of between about 0 mM to about 500 mM; and (4) detecting the separated derivatized glycan using electrospray ionization. In an embodiment, the glycans can be an O-glycan or an N-glycan.

DETAILED DESCRIPTION

Figure 1:
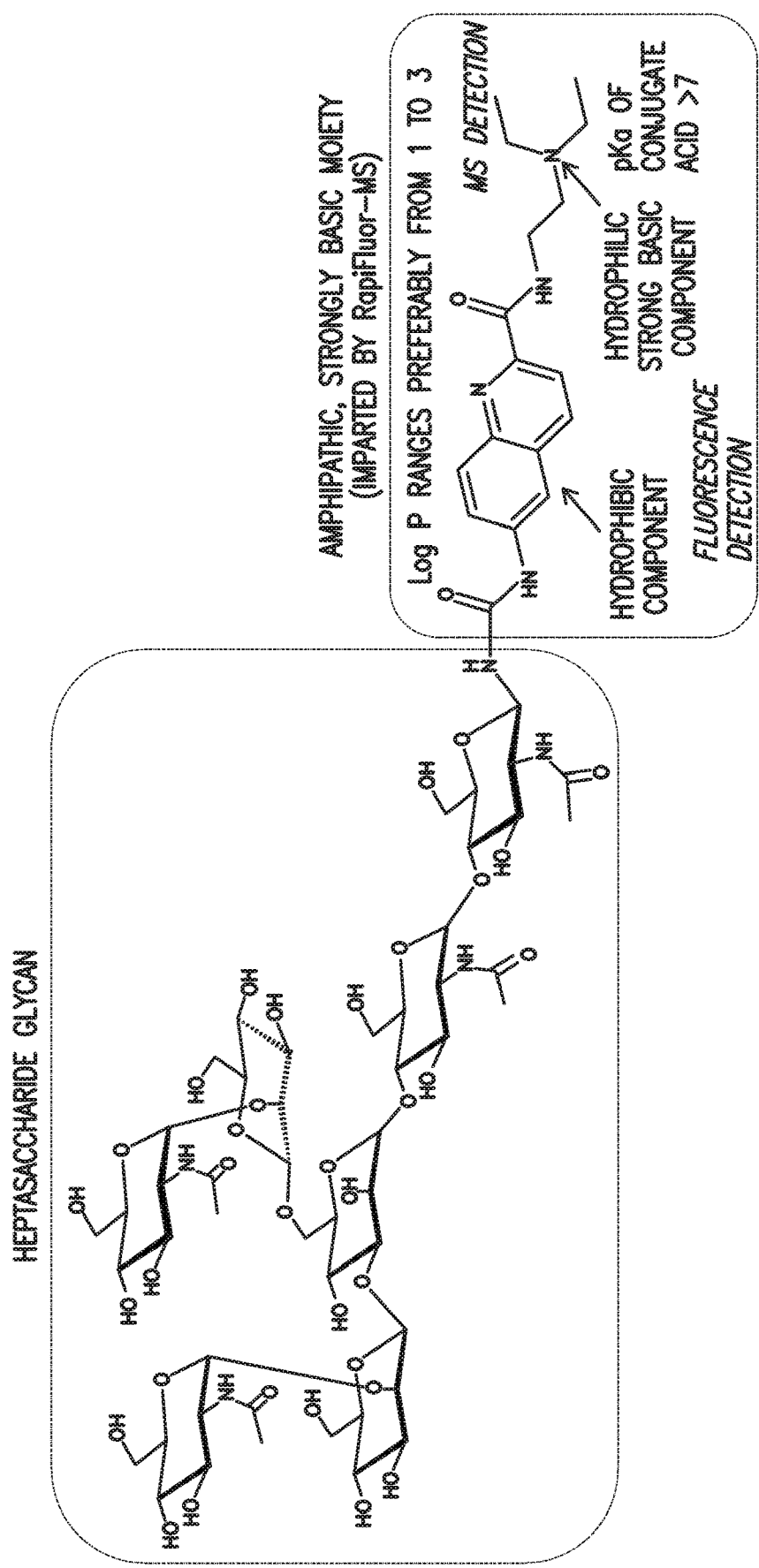
FIG. 1 shows an exemplary chemical structure of a glycan modified with an amphipathic, strongly basic moiety.

Glycans are found throughout biological systems in both a free state as well as in conjugated forms as parts of glycoproteins, glycolipids and proteoglycans. Glycans play a role in a variety of biological and physiological process. Furthermore, the structures of glycans are diverse and complex. As a result, analysis of glycan profiles can be difficult.

With recent advancements in mass spectrometry instrumentation, the combination of liquid chromatography, fluorescence and MS has gained popularity as an analytical instrument platform for routine characterization of fluorescently labeled N-linked glycans. Relative quantitation and molecular weight measurements can be done in a single analysis. Shigeo Suzuki et al., *Comparison of the Sensitivities of Various Derivatives of Oligosaccharides in LC/MS with Fast Atom Bombardment and Electrospray Ionization Interfaces,* 1006 ANAL CHEM 2073 (1996).

High performance liquid chromatography ("HPLC") can be used to analyze glycan profiles. These methods include, but are not limited to, reversed phase chromatography, ion exchange chromatography and hydrophilic interaction chromatography ("HILIC") separations. Released glycans can be separated by HILIC or, alternatively, reversed phase chromatography, using graphitic stationary phases such as porous graphitized carbon and mobile phases acidified by formic acid. In addition, glycans can be separated by capillary electrophoresis.

Upon separation, the detection process can be carried out using either an absorbance or fluorescence detector. As each labeled glycan is eluted from the chromatographic column after separation, its presence and quantity is detected by a mass spectrometer and/or by its optical properties. The sensitivity of the assay, of course, depends upon the strength of the signal produced. Methods for analyzing glycans have become considerably sophisticated. Exemplary analytical instrumentation and associated chromatographic devices that can analyze glycans include, but is not limited to, capillary electrophoresis ("CE"), high-performance anion exchange chromatography coupled with electrochemical detection ("HPAEC-PED"), hydrophilic interaction chromatography with fluorescence detection ("HILIC-LC/FLR"), reversed-phase liquid chromatography coupled with mass spectrometry ("RPLC/MS"), and matrix-assisted laser desorption/ionization mass spectrometry ("MALDI-MS.")

Notwithstanding, glycans do not ionize efficiently via electrospray ionization ("ESI") and are not readily detectable by liquid chromatography mass spectrometry ("LC-MS") alone because absorbance and fluorescence responses are quite weak. Even larger glycans, such as heavily sialylated and polysiaylated glycans, are not detected because they are extremely labile and exhibit low ionization efficiency.

Therefore, in order to increase detection sensitivity, a glycan can be converted into a derivative glycan (also referred to herein as a "labeled glycan") with a derivatization reagent. The derivatizing reagent can affect the sensitivity and accuracy of the analysis by maximizing the sensitivity, yield and stability of the derivatized glycans. As such, certain derivation reagents (also referred to herein as a "reagent" or "labeling reagent") have been shown to form stable, highly fluorescent MS derivative compounds and conjugate glycans. Selection of the labeling reagent is central to an analytical procedure.

Figure 2:
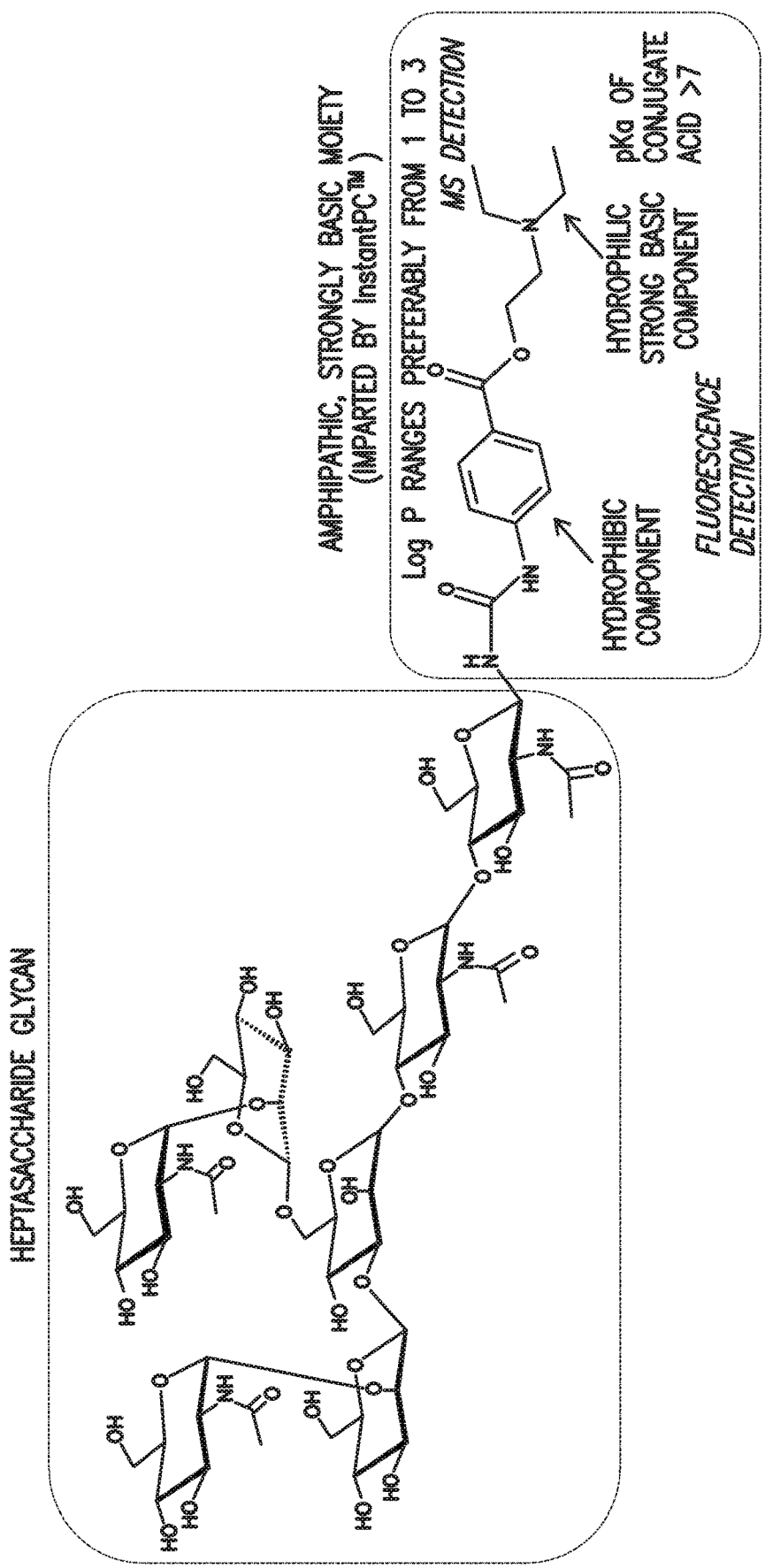
FIG. 2 shows yet another exemplary chemical structure of a glycan modified with an amphipathic, strongly basic moiety.

For example, recent work from our laboratory has demonstrated that a novel glycosylamine labeling reagent, RapiFluor-MS ("RFMS") having the chemical structure:

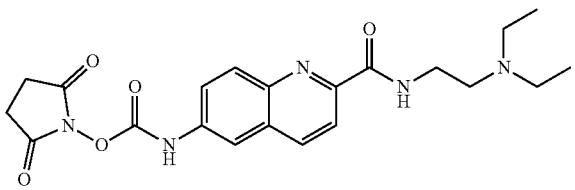 [SMILES: CCN(CC)CCNC(=O)c1ccc2cc(NC(=O)ON3C(=O)CCC3=O)ccc2n1]

can form a labeled glycan ("RFMS-labeled glycan") having enhanced MS sensitivity during HILIC analyses based on positive ion mode electrospray ionization ("ESI+"). Lauber, M. A. et al, *Rapid Preparation of Released N-Glycans for HILIC Analysis Using a Labeling Reagent that Facilitates Sensitive Fluorescence and ESI-MS Detection*, Anal Chem, 87 (10), 5401-9 (2015), incorporated herein by reference. FIGS. 1 and 2 show heptasaccharide glycan portion labeled with RFMS, such that it is modified with an amphipathic, strongly basic moiety. As described, these particular reagents (RFMS and InstantPC) incorporates an amphipathic label onto glycans that increases analyte hydrophobicity and introduces a basic residue (pKa>5), a tertiary amine. These characteristics delineate the structure of the labeled glycan that displays gas phase proton affinity. For example, RFMS-labeled glycans can show high ionization efficiencies during ESI+MS as well as correspondingly high charge state (>2+), protonated ions.

The glycan label imparted by the RFMS reagent (FIG. 1) represents only one example of an amphipathic, strongly basic moiety. Other reagents having corresponding labeling moieties that with the same characteristics can be used, including, but not limited to the labeling reagents identified in U.S. patent application Ser. No. 14/458,760 entitled Rapid Fluorescence Tagging of Glycans and Other Biomolecules with Enhanced MS Signals, pages 2, lines 4 to page 4, line 9; page 11 line 4 to page 25, line 18 and page 29, line 1 to page 30 line 10 incorporated herein by reference; U.S. Pat. No. 7,148,069, entitled Method for Analysis of Compounds With Amino Group and Analytical Reagent Therefor, at Col. 8, l. 56 to Col. 9, l. 54 and Col. 15, l. 22 to 29, incorporated herein by reference; U.S. Pat. No. 7,494,815 entitled Method and Apparatus for Analyzing Compounds with Amino Group, at Col. 7, l. 19 to Col. 11, l. 24, incorporated herein by reference; U.S. Pat. No. 8,124,792, at Col. 2, l. 13 to Col. 4, l. 5 and Col. 7, l. 11 to Col. 17, l. 20 incorporated herein by reference; and U.S. Pat. No. 5,296,599 entitled Activated Carbamates Compounds at Col. 4, l. 66 to Col. 5, l. 32 and Col. 5, l. 66 to Col. 7, l. 28, incorporated herein by reference. Each of the reagents contains amphipathic, strongly basic moieties with log P values between 0 and 5, preferably between 1 and 3, and pKa values greater than 6, preferably greater than 8. Additional exemplary reagents can contain procainamide and procaine moieties incorporated into a glycan through a secondary amine, urea, or amide linkage. See, U.S. Provisional Patent Application Nos. 62/352,724 and 62/352,734. The term moiety as used herein means a chemical functional group or plurality of chemical functional groups, including but not limited to a quinoline ring or guinoline ring combined with diethylaminoethyl group. Additional exemplary moieties useful in connection with the present methods and systems are described in Application No. PCT/US2012/057996 published as WO 2013/049622, at page 21, line 9 through page 30, line 10, incorporated herein by reference; US Pub. No. 2016/0139136, page at 2, line 9 through page 4, line 8 (referenced in Formula I as "FL-R$^3$"), incorporated herein by reference.

Glycans labeled with the reagents having amphipathic, strongly basic moieties can be readily amenable to HILIC (as well as ESI+MS) when conventional HILIC buffers such as ammonium formate buffer titrated to pH 4.4, are used for the mobile phases. Notwithstanding, unexpected problems have been faced in utilizing labeled glycans in reversed phase liquid chromatography ("RPLC") under certain conventional RPLC electrospray conditions. For example, sometimes labeled glycans are strongly retained and insufficiently resolved. Therefore, described herein are methods and systems having solution conditions that can be used to facilitate the detection of labeled glycans during separations based on reversed phase liquid chromatography, specifically detection by ESI-MS analysis of glycans labeled with amphiphatic strongly basic moieties, wherein glycans are electrosprayed from a solution having pH between 2.8 and 7, or about 3 and about 6.

General methodology for an efficient and effective analysis of the derivatized glycan includes three closely related processes: (1) formation of derivatized glycan in the sample; (2) separation of the derivatized glycans; and (3) detection of the separated derivatized glycans. Formation of the derivatized glycan is performed through one of several chemical reactions by reacting a biological sample containing the glycan (or glycan having been already separated from the biological sample) with one or more reagents to yield a derivatized glycan (sometimes referred to herein as a "derivatized compound," "derivatized glycan," "labeled glycan," "RFMS-labeled glycan" or "labeled compound"). Different processes for forming the derivatized glycan include, but are not limited to, rapid tagging or reductive amination. Such processes are described in PCT/2015/057848, published as WO 2016/069664 and particularly as summarized at pages 2 and 4, incorporated herein by reference. Formation of an effective labeled glycan, however, is only the first step.

Separation processing of the labeled glycan is based upon the differences in the chemical structure of the derivatized glycan. See e.g., Qing, Y. et al., *A Rapid Sample Preparation Method for Mass Spectrometric Characterization of N-Linked Glycans*, Rapid Commun. Mass Spectrom 2005 19 2331-2336 (2008). Labeled glycans can differ from each other in the same way that the chemical structures of the precursor compounds differ. In the present methods, the labeled glycan is separated so that the detector signal can be correctly related to the concentration of each glycan. As noted above, in these methods, the labeled glycan is separated chromatographically either solely or partially by a reversed-phase retention mechanism and subsequently detected by electrospray ionization.

Generally, in-source fragmentation ("ISF") is directly related with the desolvation and activation energy at the interface of electrospray ionization ("ESI") source. The desolvation/activation energy is controlled by the cone voltage (also called nozzle-skimmer voltage, or declustering voltage). Higher desolvation/activation energy can enhance ion yield but simultaneously facilitate ISF due to elevated ion energy, which compromises the final ion yield. In practice, researchers can optimize the ESI-MS desolvation process by balancing these two inversely proportional factors to maximize ion gain.

When not separated by HILIC, glycans released from a biological mixture are often separated by reversed-phase liquid chromatography and other chromatographic methods using a chromatographic device. For reversed-phase chromatography, the chromatographic devices can be graphitic stationary phases, including but not limited to, porous graphitized carbon, and strongly acidic mobile phases that are typically based only on formic acid. West, C. et al., *Porous Graphitic Carbon: a Versatile Stationary Phase for Liquid Chromatography, J Chromatogr A* 1217 (19), 3201-16 (2010); Ruhaak, L. R., *Glycan Labeling Strategies and Their Use in Identification and Quantification, Anal Bioanal Chem* 397 (8), 3457-81 (2010). When subject to electrospray ionization in formic acid based mobile phases, however, labeled glycans modified with strongly basic residues are prone to degradation via in-source fragmentation—even when relatively gentle MS source conditions are employed.

Figure 3A:
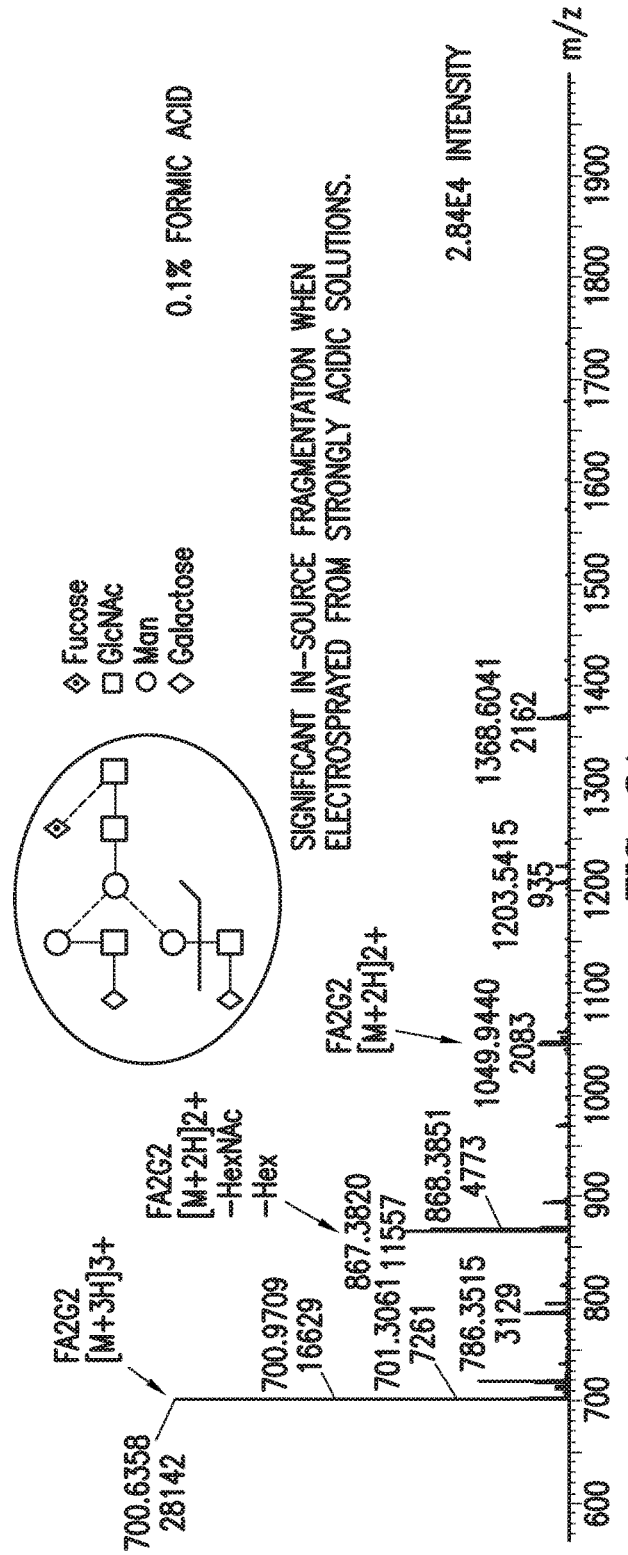
FIG. 3A is an ESI mass spectrum for RFMS labeled FA2G2 glycan as electrosprayed from a solution comprising 0.1 percent formic acid in 20 percent acetonitrile.
Figure 3B:
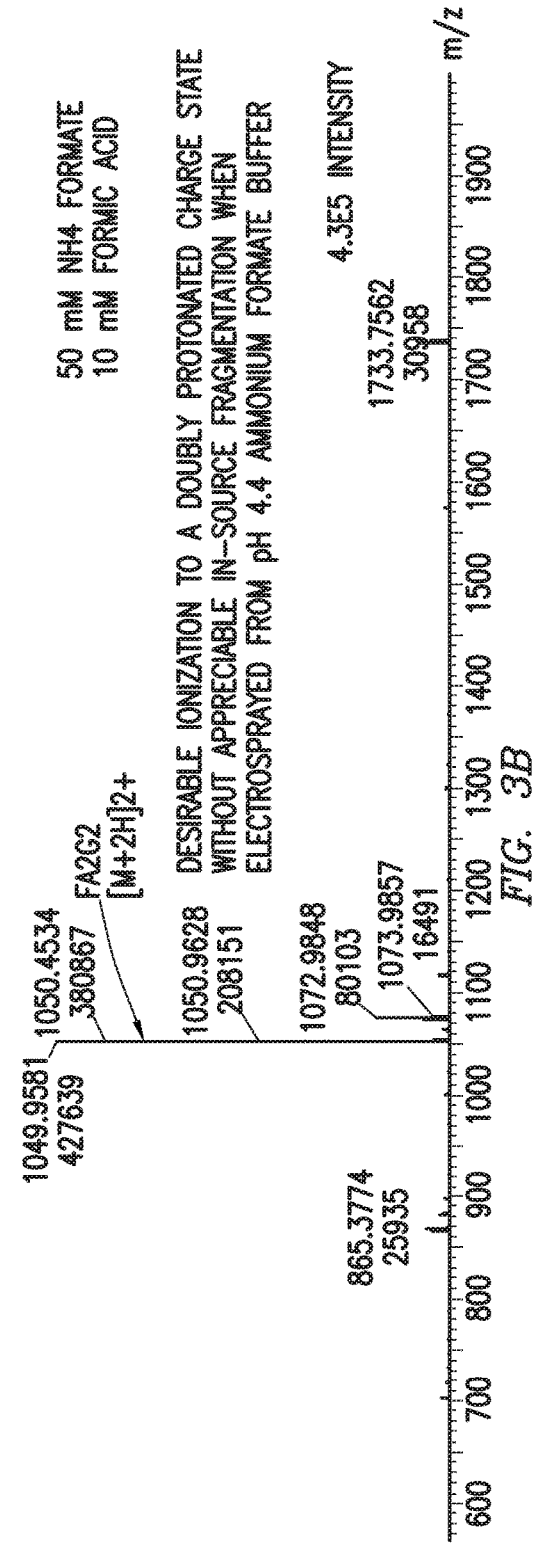
FIG. 3B is an ESI mass spectrum for a labeled FA2G2 glycan as electrosprayed from a solution comprising approximately 20:80 acetonitrile and 50 mM ammonium formate having a pH of 4.4.
Figure 3C:
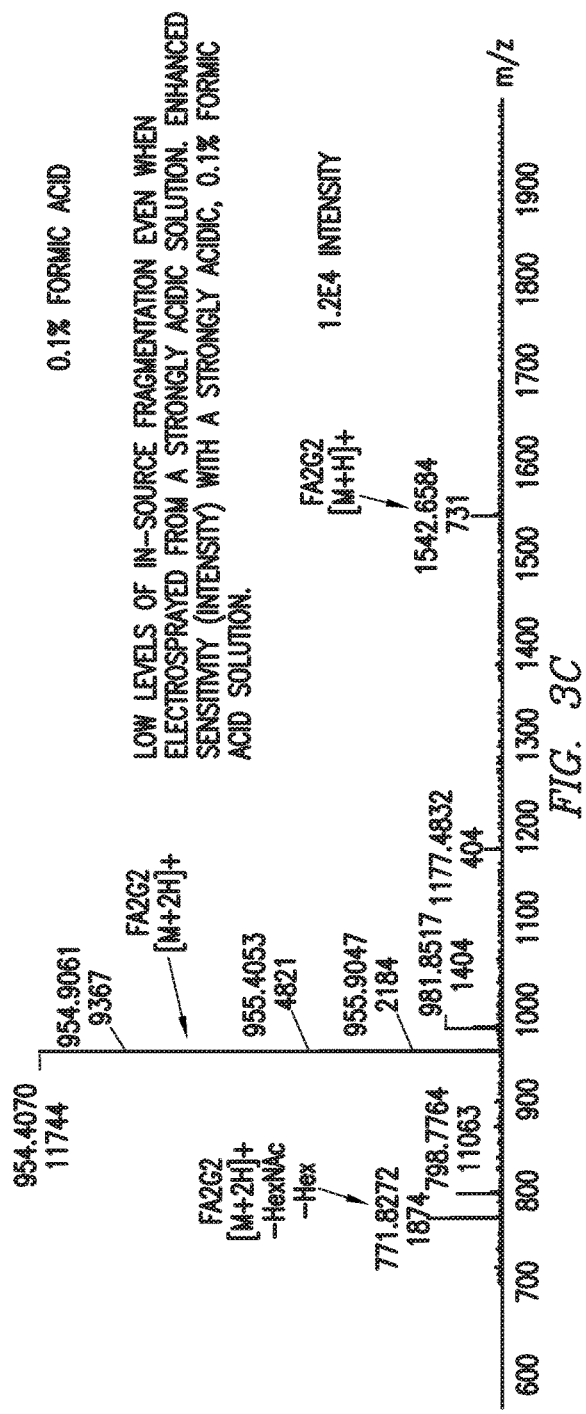
FIG. 3C is an ESI mass spectrum for 2-AB labeled FA2G2 glycan as electrosprayed from strongly acidic ESI+ conditions comprising 0.1 percent formic acid in 20 percent acetonitrile and stabilized by solutions buffered with volatile ammonium salts between pH 3 and pH 6.
Figure 3D:
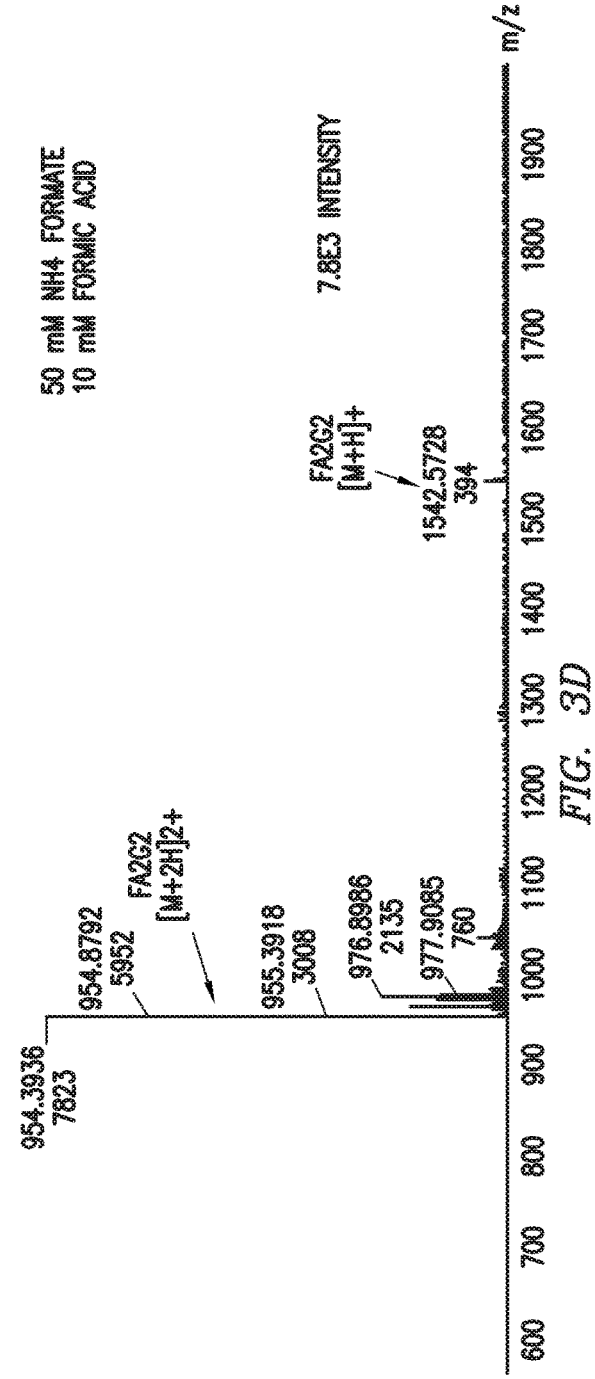
FIG. 3D is an ESI mass spectrum for the 2-AB labeled FA2G2 glycan as electrosprayed from a solution comprising approximately 20:80 acetonitrile and 50 mM ammonium formate having a pH of 4.4.

FIGS. 3A and 3B show that RFMS-labeled N-glycans can be labile when electrosprayed from strongly acidic ESI+ conditions but stabilized by solutions buffered with volatile ammonium salts between pH 3 and 6. By way of comparison, in FIG. 3A, an ESI mass spectrum is shown for a RFMS-labeled FA2G2 glycan electrosprayed from a solution consisting of approximately 0.1% formic acid in 20% acetonitrile. In FIG. 3B, the ESI mass spectrum is shown for a RFMS-labeled FA2G2 glycan electrosprayed from a solution comprising approximately 20:80 acetonitrile:50 mM ammonium formate pH 4.4. In these figures, "-HexNAc" denotes a loss of a N-acetylated hexosamine residue. "-Hex" denotes a loss of a hexose residue. Glycans are named according to the Oxford notation.

FIG. 3A demonstrates a mass spectrum for RFMS-labeled FA2G2 obtained by electrospraying glycans out of a solution comprising approximately 0.1% formic acid in 20% acetonitrile. Significant in-source fragmentation occurred. Notice that charging occurred up to a triply protonated charge state. More problematically, the spectrum shows significant levels of ions resulting from in-source fragmentation. This has been found to occur even with the use of source potentials and temperatures comparatively lower than source parameters previously published as optimal conditions for RFMS-labeled N-glycans. See e.g., Lauber, M. A.; et al., *Rapid Preparation of Released N-Glycans for HILIC Analysis Using a Labeling Reagent that Facilitates Sensitive Fluorescence and ESI-MS Detection, Anal Chem* 2015, 87 (10), 5401-9, at 5407 to 5408, incorporated herein by reference. Comparatively, a higher pH solution stabilizes the labeled glycan against ISF. As shown in FIG. 3B, ESI mass spectrum for a RFMS-labeled FA2G2 glycan electrosprayed from a solution consisting of approximately 20:80 acetonitrile:50 mM ammonium formate pH 4.4. This mass spectrum shows desirable ionization to a doubly protonated charge state without appreciable in-source fragmentation when electrosprayed from pH 4.4 ammonium formate buffer.

As described herein, the present methodologies provide solution conditions that can be used to facilitate the liquid chromatography mass spectrometry ("LC-MS") analysis of glycans modified with amphipathic, strongly basic moieties. RFMS-labeled FA2G2 has been found to show a much higher signal-to-noise, lower background mass spectrum when electrosprayed from a solution comprising approximately 20:80 acetonitrile: 50 mM ammonium formate/10 mM formic acid pH 4.4. These effects are counter to previous observations for glycans labeled with a conventional fluorophore label, such as 2 aminobenzamide ("2-AB"). See, FIGS. 3A and 3B.

Glycans labeled with amphipathic, strongly basic residues can be be forced to inordinately high charge states and low m/z values when electrosprayed out of strongly acidic solutions (pH≤3). It appears that the high charge state, low m/z species is inherently unstable and prone to in-source fragmentation. This problem can be avoided through the use of solution conditions described herein.

As such upon investigating this phenomenon, we have discovered that glycans labeled with amphipathic, strongly basic residues are optimally electrosprayed using pH 3 to pH 6 solutions that have been buffered with volatile components, including but not limited to ammonium formate, formic acid, ammonium acetate, and/or acetic acid. Use of a volatile pH 3 to pH 6 buffer during the LC-ESI+MS analyses of glycans, especially those glycans labeled with amphipathic, strongly basic residues, can lead to stabilization of the labeled glycan. The solutions and solution conditions provided herein are novel for reversed-phase LC-MS and direct infusion MS of glycans labeled with amphipathic, strongly basic residues. Glycans labeled with amphipathic, strongly basic residues have been shown to have a propensity to undergo in-source fragmentation. The solutions taught herein can be combined with more than one liquid chromatography technique. For example, the solution conditions can be combined with conventional reversed phase chromatography and mixed mode reversed phase chromatography. Mixed mode chromatography can be typified by the combination of ion exchange retention with hydrophobicity-based retention mechanisms if reversed-phase liquid chromatography. Accordingly, stabilization of the labeled glycan during ESI is implemented when at least one mechanism of the separation process is based on a reversed-phase retention mechanism.

The term reversed-phase as used herein describes the chromatography mode that is just opposite of normal-phase HPLC. In normal-phase HPLC, the stationary phase is polar and retains compounds of the mobile phase having similar polarity. Compounds whose polarity is similar to that of the mobile phase will be preferentially attracted to it and move faster through the stationary phase. In this way, based upon differences in the relative attraction of each compound for each phase, a separation is created by changing the speeds of the analytes.

Stated differently, in normal phase chromatography, the stationary phase is hydrophilic and therefore has a strong affinity for hydrophilic molecules in the mobile phase. Thus, the hydrophilic molecules in the mobile phase tend to bind (or "adsorb") to the column, while the hydrophobic molecules pass through the column and are eluted first. In normal phase chromatography, hydrophilic molecules can be eluted from the column by increasing the polarity of the solution in the mobile phase.

Reversed-phase chromatography (also called "RPC," "reverse-phase chromatography," "reversed phase liquid chromatography," "RPLC" or "hydrophobic chromatography") is a chromatographic method that uses a hydrophobic stationary phase. RPC refers to liquid (rather than gas) chromatography. Historically, the introduction of a technique using alkyl chains covalently bonded to the solid support created a hydrophobic stationary phase or chromatographic device, which has a stronger affinity for hydrophobic compounds. The use of a hydrophobic stationary phase can be considered the opposite, or "reverse", of normal phase chromatography and therefore, the term "reversed-phase chromatography." Reversed-phase chromatography typically employs a polar (aqueous) initial mobile phase. As a result, hydrophobic molecules in the polar mobile phase tend to adsorb to the hydrophobic stationary phase, and hydrophilic molecules in the mobile phase will pass through the column and are eluted first. Hydrophobic molecules can be eluted from the column by decreasing the polarity of the mobile phase using an organic (non-polar) solvent, which reduces hydrophobic interactions. The more hydrophobic the molecule, the more strongly it will bind to the stationary phase, and the higher the concentration of organic solvent that will be required to elute the molecule. Mathematical and experimental considerations used in other chromatographic methods can also apply to reversed phase chromatography (for example, the separation resolution is dependent on the length of the column).

Theoretically, any inert non-polar substance or chromatographic device that achieves sufficient packing can be used for reversed-phase chromatography as the chromatographic device for reversed phase chromatography is a hydrophobic stationary phase. One such chromatographic device includes a column having an octadecyl carbon chain (C18)-bonded silica (USP classification L1). Other chromatographic devices include C8-bonded silica columns (L7-166 columns), pure silica columns (L3-88 columns), cyano-bonded silica columns (L10-73 columns) and phenyl-bonded silica columns (L11-72 columns). Note that C18, C8 and phenyl-bonded silica are dedicated reversed-phase resins, while cyano columns can be used in a reversed-phase mode depending on analyte and mobile phase conditions. Not all C18 columns have identical retention properties. Surface functionalization of silica can be performed in a monomeric or a polymeric reaction with different short-chain organosilanes used in a second step to cover remaining silanol groups (end-capping). While the overall retention mechanism remains the same, subtle differences in the surface chemistries of different stationary phases will lead to changes in selectivity. Columns can have different polarity. For example, PFP is pentafluorophenyl. CN is cyano. NH2 is amino. ODS is octadecyl or C18. ODCN is a mixed mode column of C18 and nitrile. SCX is strong cationic exchange substrate used for separation of organic amines. SAX is strong anionic exchange used for separation of carboxylic acid compounds.

In addition, mixtures of water or aqueous buffers and organic solvents can be utilized to elute analytes from a reversed-phase column. The solvents must be miscible with water, and the most common organic solvents used are acetonitrile, methanol, and tetrahydrofuran ("THF"). Other solvents can be used such as ethanol or 2-propanol (isopropyl alcohol). Elution can be performed isocratically where the water-solvent composition does not change during the separation process or by using a solution gradient (the water-solvent composition changes during the separation process, usually by decreasing the polarity). The pH of the mobile phase can have an important role on the retention of an analyte and can change the selectivity of certain analytes. Charged analytes can be separated on a reversed-phase column by the use of ion-pairing (also called ion-interaction). This technique is known as reversed-phase ion-pairing chromatography.

With reversed-phase stationary phases bonded with C18, separations tend to produce problematic co-elutions, given that there is often poor selectivity among glycan structures differing with respect to net charge. N-glycans that have been released from glycoproteins are quite different unto themselves. In particular, released N-glycans exhibit different charge characteristics than peptides, as they will generally contain only neutral or acidic hydrophilic residues. The acidic residues in released N-glycans, and their carboxylic acids or phospho-groups, significantly impact the characteristic and net charge state of glycan species. Glycans containing more acidic residues will have greater negative net charge. Similarly, these acidic species are often correlated with the efficacy of a biopharmaceutical.

Furthermore, chromatographic devices such as those described in US Patent Pub. No. 2013/03199086, provide multimodal chromatographic media (retention mechanism) and methods of analyzing glycans that provide high resolution between different biological macromolecules, unique selectivity based on size, composition, structure (e.g., isomerism, linkages) and/or charge. These types of columns allow the macromolecules eluted from the media to be detected by standard methodology (e.g., mass spectrometry, fluorescence detection) with no, or minimal, clean up or purification post-analysis and pre-detection (e.g., fluorescent tagging). Furthermore, to achieve sufficient sensitivity and selectivity for the complete separation of glycans, particularly N-glycans, chromatographic devices having high purity chromatographic materials ("HPCMs") comprising a chromatographic surface can be used. Here, the chromatographic surface (retention mechanism) has a hydrophobic surface group and one or more ionizable modifiers. Such HPCMs are described in U.S. Patent Application No. 62/326,783 filed Apr. 24, 2016 unpublished, pages 5 and 6, incorporated herein by reference.

In the present methods, the solution can be buffered with ammonium formate, formic acid, ammonium acetate and/or acetic acid and the like. The ionic strength of the mobile phase at which glycans elute and are electrosprayed can range from infinitely low and near 0 mM up to about 500 mM, and between about 1 and about 100 mM. This phenomenon can be attributable to a counter ion than can pair with glycan residues. In that way, an aspect of the methodologies presented herein is the use of a volatile component, such as an amine compound at pH 3 to 6 conditions. Likewise, while the separation of labeled glycans is described herein in an acetonitrile/water mobile phase systems, other solvents can be utilized and paired together in mobile phase systems, including but not limited to, methanol, isopropanol, butanol, n-propanol, and tetrahydrofuran. The volatile component is an amine, including but not limited to, ammonia, diethylamine, or triethylamine. In an embodiment, the extreme charging that is evident in the mass spectra of a RFMS-labeled glycan electrosprayed out of strongly acidic conditions could be purposely exploited for analytical reasons, for instance to glean compositional or structural information. This aspect can be used in connection with any glycan labeled with an amphipathic, strongly basic moiety.

Example I

Electrospray Ionization Mass Spectrometry (ESI-MS) of Glycans Labeled with RapiFluor-MS Versus 2-AB RFMS and 2-AB labeled N-glycans were prepared from human IgG (Sigma 14506) according to previously published conditions. See e.g., Lauber, M. A.; Yu, Y. Q.; Brousmiche, D. W.; Hua, Z.; Koza, S. M.; Magnelli, P.; Guthrie, E.; Taron, C. H.; Fountain, K. J., *Rapid Preparation of Released N-Glycans for HILIC Analysis Using a Labeling Reagent that Facilitates Sensitive Fluorescence and ESI-MS Detection*, Anal Chem 87 (10), 5401-9 (2015).

The labeled FA2G2 glycans were then electrosprayed at a flow rate of 200 μL/min from a solution consisting of approximately 0.1% formic acid in 20% acetonitrile or a solution consisting of approximately 80:20 acetonitrile:50 mM ammonium formate pH 4.4. Mass spectra were acquired using a Waters Synapt G2-S mass spectrometer. Comparatively gentle MS conditions were employed in these analyses that contrast the differences between electrospray conditions as shown in FIGS. 3A, 3B, 3C and 3D.

Immediately below were the mass spectrometry conditions utilized:

| | |
|---|---|
| Polarity | ES+ |
| Acquisition: | 700-2000 m/z (1 Hz) |
| Capillary (kV) | 3 |
| Source Temperature (° C.) | 100 |
| Sampling Cone | 30 |
| Source Offset | 50 |
| Desolvation Temperature (° C.) | 300 |
| Desolvation Gas Flow (L/Hr) | 800 |
| Nebuliser Gas Flow (Bar) | 7.0 |

We claim:

1. A solution for use in electrospray ionization comprising: a plurality of glycans modified to include an amphipathic, strongly basic moiety comprising a basic residue of pKa>5; the solution buffered with volatile components comprising ammonium formate and formic acid, wherein the solution has a pH between about 3 to about 6, and an ionic strength of between about 1 mM to about 500 mM.

2. The solution of claim 1, further comprising a solvent.

3. The solution of claim 2, wherein the solvent is selected from the group consisting of acetonitrile, methanol, tetrahydrofuran, ethanol or isopropyl alcohol.

4. The solution of claim 1, wherein the plurality of glycans modified to include the amphipathic, strongly basic moiety have a log P value between about 1 and about 3.

5. The solution of claim 4, wherein the amphipathic, strongly basic moiety has a basic residue having a pKa value greater than 6.

6. The solution of claim 1, wherein the basic residue is a tertiary amine.

7. The solution of claim 1 wherein the amphipathic, strongly basic moiety is imparted by

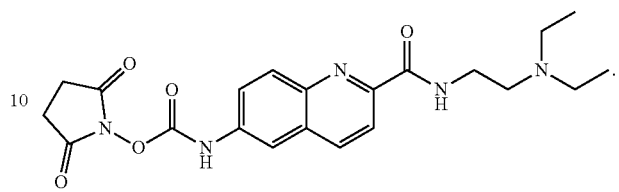

8. The solution of claim 1, wherein the glycan is an N-glycan or an O-glycan.

9. The solution of claim 1, wherein the amphipathic, strongly basic moiety is imparted by

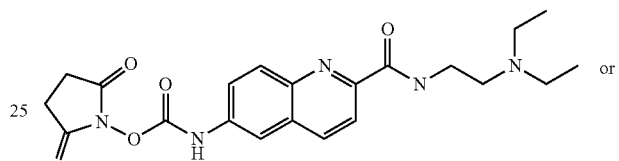

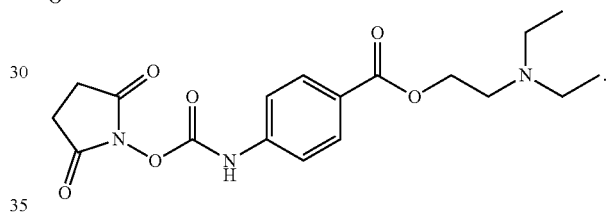

10. A chromatographic system for glycan analysis comprising:
a solution having a plurality of glycans modified to include an amphipathic, strongly basic moiety having a basic residue of pKa>5, and volatile components comprising ammonium formate and formic acid, the solution having a pH between about 3 to about 6, and ionic strength of between about 1 mM to about 500 mM; and
a chromatographic device comprising a hydrophobic stationary phase.

11. The chromatographic system of claim 10 wherein the plurality of glycans are N-glycans and/or O-glycans.

12. The chromatographic system for glycan analysis of claim 10, wherein the chromatographic device comprises a reversed-phase retention mechanism.

13. The chromatographic system for glycan analysis of claim 10, wherein the chromatographic device is a combination of reversed-phase chromatography and mixed mode reversed-phase chromatography.

14. A method of detecting a glycan comprising the steps of:
providing a sample wherein the sample comprises glycans;
forming derivatized glycans in the sample by modifying the glycans to include an amphipathic, strongly basic moiety having a basic residue of pKa>5;
separating the derivativized glycans in a chromatographic device and in a solution comprising one or more volatile components comprising ammonium formate and formic acid, the solution having a pH between about 3 to about 6, and ionic strength of between about 1 mM to about 500 mM; and detecting the separated derivatized glycan using electrospray ionization.

15. The method of claim 14, wherein the glycan is an O-glycan or an N-glycan.

16. The chromatographic system of claim 10, wherein the basic residue is a tertiary amine.

17. The chromatographic system of claim 10, wherein the amphipathic, strongly basic moiety is imparted by

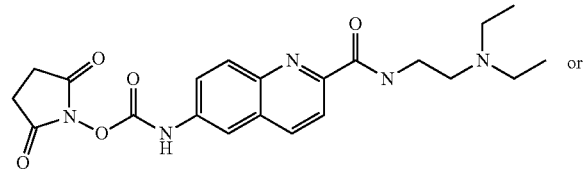

or

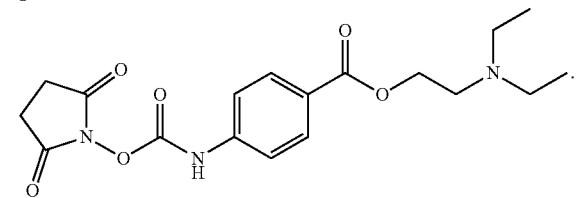

18. The chromatographic system of claim 10, wherein the solvent comprises acetonitrile, methanol, tetrahydrofuran, ethanol or isopropyl alcohol.

19. The method of claim 14, wherein the basic residue is a tertiary amine.

20. The method of claim 14, wherein the amphipathic, strongly basic moiety is imparted by

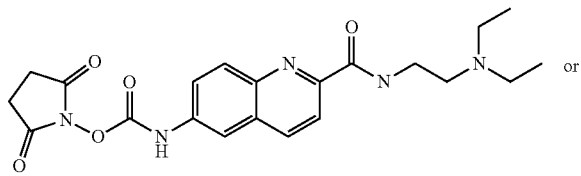

or

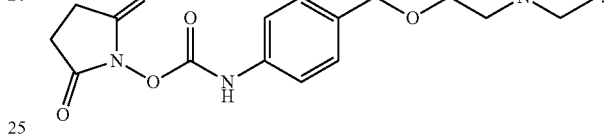

* * * * *